United States Patent [19]

Pirrung et al.

[11] Patent Number: 5,486,633
[45] Date of Patent: Jan. 23, 1996

[54] PHOTOCHEMICALLY-REMOVABLE SILYL PROTECTING GROUPS

[75] Inventors: Michael C. Pirrung, Houston, Tex.; Yong Rok Lee, Durham, N.C.

[73] Assignee: Duke University, Durham, N.C.

[21] Appl. No.: 339,216

[22] Filed: Nov. 10, 1994

[51] Int. Cl.$^6$ .................... C07F 7/08; C07F 7/10
[52] U.S. Cl. .................... 556/410; 556/413; 556/424; 556/426; 556/429; 556/449; 549/214
[58] Field of Search ..................... 556/410, 413, 556/424, 426, 429, 449; 549/214

[56] References Cited

U.S. PATENT DOCUMENTS

| | | | |
|---|---|---|---|
| 3,767,690 | 10/1973 | Speier | 556/413 |
| 4,132,702 | 1/1979 | Schmidt et al. | 556/413 X |
| 4,558,146 | 12/1985 | Kanner et al. | 556/410 |
| 4,801,659 | 1/1989 | Leslie | 556/413 X |
| 4,855,078 | 8/1989 | Leslie | 556/413 X |
| 5,143,854 | 9/1992 | Pirrung et al. | 436/518 |
| 5,210,247 | 5/1993 | Haberle et al. | 556/413 |

OTHER PUBLICATIONS

Pirrung et al, "Photochemically–Removable Silyl Protecting Groups", J. Org. Chem. 58:6961–6963 (1993).

Fodor et al, "Multiplexed biochemical assays with biological chips", Nature 364:555–556 (1993).

Lew et al, "Photochemical Protodesilylation of 2–R$_3$Si–1,3–dimethoxybenzenes. Direct Observation of β–Silyl–Substituted Cyclohexadienyl Cations", J. Am. Chem. Soc. 115:11516–11520 (1993).

Fodor et al, "Light–Directed, Spatially Addressable Parallel Chemical Synthesis", Science 251:767–773 (1991).

Horne et al, "Recognition of Mixed–Sequence Duplex DNA by Alternate–Strand Triple–Helix Formation", J. Am. Chem. Soc. 112:2435–2437 (1990).

*Primary Examiner*—Paul F. Shaver
*Attorney, Agent, or Firm*—Nixon & Vanderhye

[57] ABSTRACT

The present invention relates, in general, to photochemically removable protecting groups, and, in particular, to the use of styrylsilyl groups to protect reactive functional groups, such as, hydroxyl, amino and thiol groups.

10 Claims, 3 Drawing Sheets

PHOTOCHEMICALLY-REMOVABLE SILYL PROTECTING GROUPS

This invention was made with Government support under Grant No. GM 46720 awarded by the National Institutes of Health. The Government has certain rights in the invention.

FIELD OF THE INVENTION

The present invention relates, in general, to photochemically removable protecting groups, and, in particular, to the use of styrylsilyl groups to protect reactive functional groups, such as, hydroxyl, amino and thiol groups.

BACKGROUND

Photochemically-removable groups have many applications in bioorganic chemistry. Besides providing deprotection that can be accomplished under conditions that leave most other protecting groups untouched (Pillai, V. N. R, Organic Photochemistry 3:225 Synthesis (1980)), photochemically removable groups can also be used in the technique of caging (Adams et al, J. Am. Chem. Soc. 111:7957 (1989)) wherein a biological molecule is rendered both inactive and membrane-permeable by the protecting group. Once located inside a cell or an enzyme active site (Schlichting et al, Proc. Natl. Acad. Sci. USA 86:7687 (1989)), the protecting group can be released on a time scale much faster than that of the biological or enzymatic process, permitting the study of the time evolution of the phenomena. Photoremovable groups are also key to the novel technique of light-directed synthesis. This technique is used to prepare large arrays consisting of thousands of biopolymer sequences (see Fodor et al, Science 251:767 (1991) and U.S. Pat. No. 5,143,854).

Many of the photoremovable groups currently in use are based on nitrobenzyl photochemistry that produces a byproduct nitrosocarbonyl compound. This substance can create problems with development of intensely absorbing solutions during deprotection and reaction with functional groups such as amines. Nitrobenzylethers can also be difficult to form from alcohols, a functional group commonly requiring protection (Pirrung et al, Bioorg. Med. Chem. Lett. 2:1489 (1992)). The present invention overcomes the problems of prior protecting reagents and provides excellent photochemically removable agents for the protection of functional groups, including primary and secondary alcohols.

OBJECTS AND SUMMARY OF THE INVENTION

It is a general object of the invention to provide a reagent that can be used to protect reactive moieties, including hydroxyl, amino and thiol groups, and that can be removed photochemically.

It is a specific object of the invention to provide a silyl protecting group, specifically, a styrylsilyl compound, that, upon irradiation, is readily removed.

It is a further object of the invention to provide a method of protecting reactive functional groups, including alcohols, using photoreactive styrylsilyl reagents.

In a first embodiment, the present invention relates to a photochemically-removable silyl protecting agent of the Formula (I):

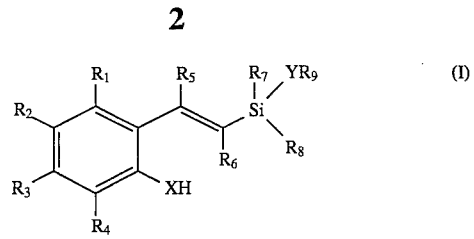

wherein:
$R_1$–$R_6$ are, independently, hydrogen, alkyl, O-alkyl, N-alkyl, S-alkyl, aryl, heteroaryl or halogen;
$R_7$–$R_8$ are alkyl;
$YR_9$ is a leaving group; and
X is S, O or NH.

In a second embodiment, the present invention relates to a method of protecting a reactive functional group. The method comprises reacting the abovedescribed agent with the functional group under conditions such that a styrylsilyl derivative of the functional group is formed. The present invention also relates to the thus protected product.

Further objects and advantages of the invention will be clear from the description that follows.

Spectral data for "5": $^1$H NMR (CDCl$_3$) δ 0.33 (s, 6H), 5.89 (d, J=14.4, 1H), 6.87–7.13 (m, 4H), 7.23 (d, J=14.4, 1H); IR (neat): 3061, 2995, 2974, 1599, 1552, 1480 1449, 1273, 1263, 1101, 1030, 923, 795, 752 cm$^{-1}$; MS (m/z, CI) 177 (M$^+$ + 1); HRMS (CI): calcd. for C$_{10}$H$_{13}$OSi, 177.0736, found 177.0726. The analogous diisopropylsiloxane derivative shows $^1$H NMR (CDCl$_3$): δ 1.02 (d, J=4.2, 6H), 1.04 (d, J=3.3, 6H), 1.06 (m, 2H), 5.84 (d, J=14.4, 1H), 6.85–7.11 (m, 4H), 7.35 (d, J=14.4, 1H); IR (neat): 2943, 2865, 1598, 1480, 1272, 1262, 1100, 920, 777, 751 cm$^{-1}$; MS (m/z, CI): 233 (M$^+$+ 1); HRMS (EI): calcd for C$_{14}$H$_{20}$OSi, 232.1283, found 232.1290.

Spectral data for "6": $^1$H NMR (600 MHz, CDCl$_3$): δ 0.24 (s, 6H), 0.81 (s, 9H), 0.93–1.93 (m, 9H), 3.72 (m, 1H), 5.21 (dd, J=11.4, 1.2 Hz, 1H) 5.69 (dd, J= 17.4, 1.2 Hz, 1H), 6.92 (m, 2H), 6.99 (dd, J=17.4, 11.4 Hz, 1H), 7.11 (ddd, J=8.1, 7.5, 1.8 Hz, 1H), 7.46 (dd, J=7.5, 1.8 Hz, 1H); IR (neat): 2946, 2867, 1598, 1552, 1484, 1452, 1255, 1088, 927, 801, 754 cm$^{-1}$; MS (m/z, CI): 333 (M$^+$+1); HRMS (EI): calcd for C$_{20}$H$_{32}$O$_2$Si 332.2171, found 332.2168.

Spectral data for "8": $^1$H NMR (600 MHz): δ 0.94 (m, 2H), 0.98 (d, J=6.6 Hz, 12H), 1.77 (br s, 1H), 2.25 (s, 3H), 5.85 (d, J=15.6 Hz, 1H), 6.98 (dd, J= 7.8, 1.2 Hz, 1H), 7.20 (dd, J=7.8, 6.6 Hz, 1H), 7.28 (ddd, J=7.8, 7.8, 1.2 Hz, 1H), 7.35 (d, J=15.6, Hz, 1H), 7.36 (d, J=6.6 Hz, 1H); IR (neat): 3444, 2949, 2885, 1785, 1603, 1485, 1371, 1204, 1091, 846, 757 cm$^{-1}$ MS (m/z, CI): 293 (M$^+$+1), 275; (M$^+$+1− H$_2$O); HRMS (EI): calcd for C$_{16}$H$_{24}$O$_3$Si 292.1494, found 292.1494.

Figure 2:
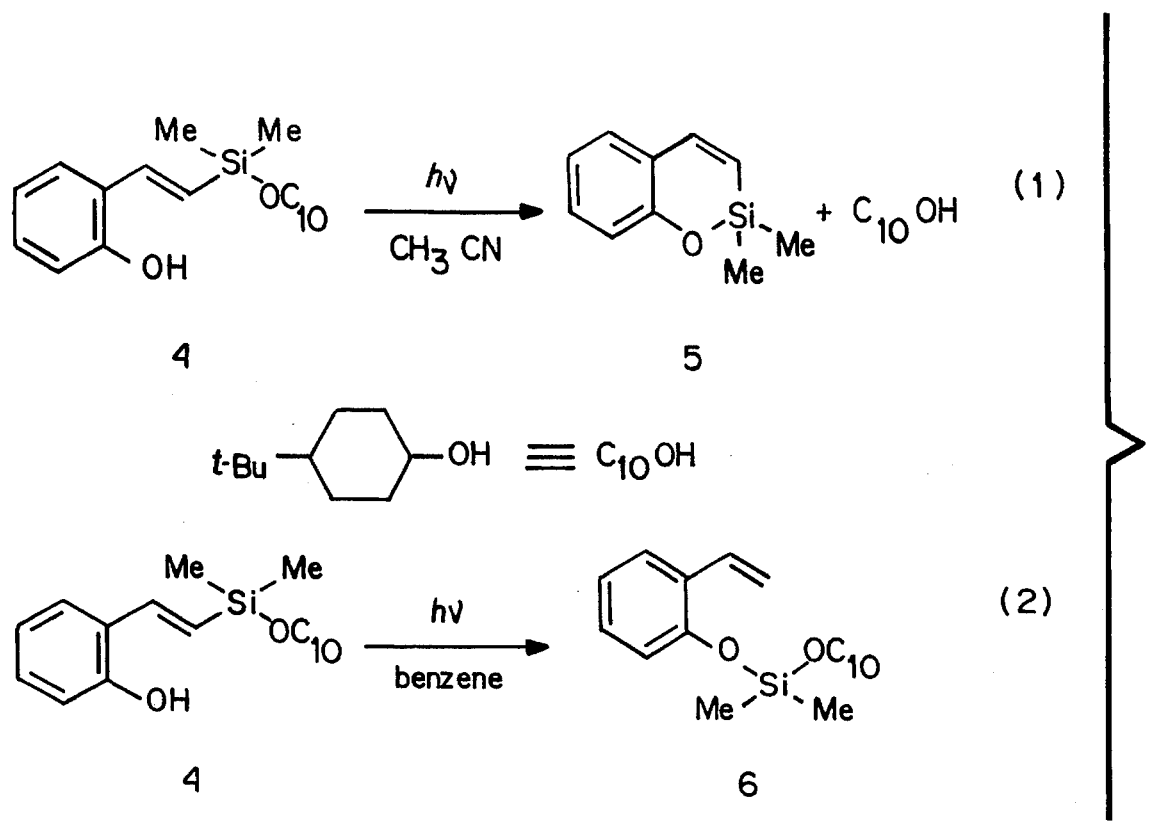

FIG. 2. Solvent dependence of photochemistry of (hydroxystyryl) silyl ethers.

Figure 3:
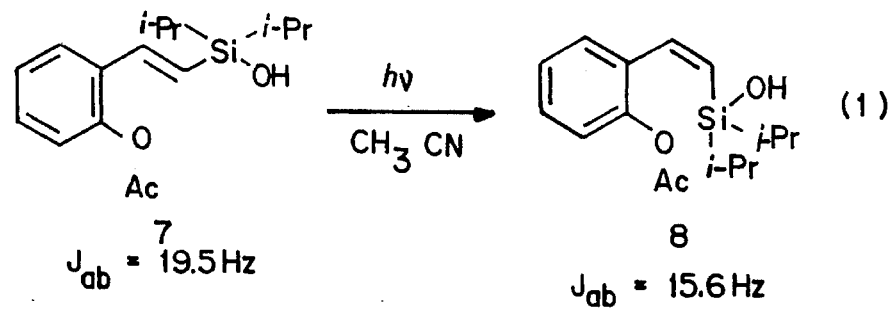
Figure 3:
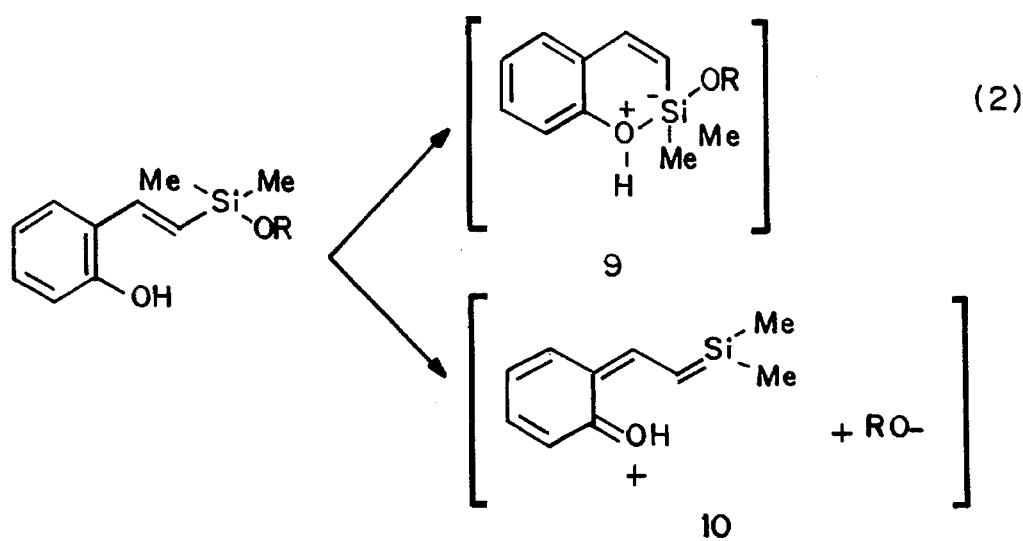
Figure 3:
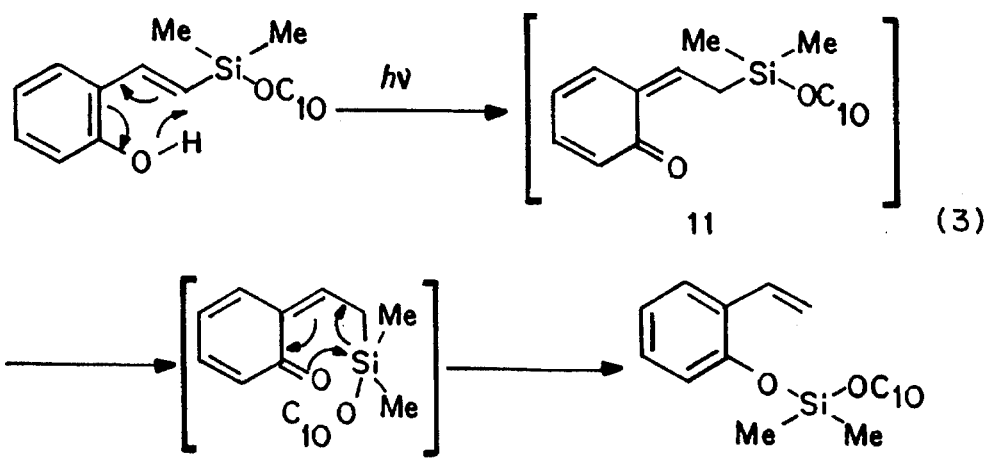

FIG. 3. Mechanism of deprotection.

DETAILED DESCRIPTION OF THE INVENTION

The present invention relates to photochemically-removable silyl protecting groups and to methods of protecting reactive functional groups (eg, hydroxyl, amino and thiol groups) using same.

Protecting agents suitable for use in the invention are of the Formula I:

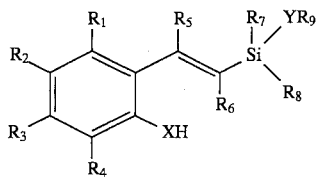

wherein:
$R_1$–$R_6$ are, independently, hydrogen, alkyl, O-alkyl, N-alkyl, S-alkyl, aryl, heteroaryl or halogen;
$R_7$–$R_8$ are alkyl;
$YR_9$ is a leaving group; and
X is S, O or NH;
or salts thereof.

In a preferred embodiment,
$R_1$–$R_6$ are, independently, hydrogen, $(C_1$–$C_4)$alkyl, O-$(C_1$–$C_4)$alkyl, N-$(C_1$–$C_4)$alkyl, S-$(C_1$–$C_4)$alkyl, phenyl, Br or Cl;
$R_7$–$R_8$ are $(C_1$–$C_4)$alkyl;
$YR_9$ is a halogen or Y is N, S or O and $R_9$ is $(C_1$–$C_4)$ alkyl or di$(C_1$–$C_4)$alkyl, as appropriate; and
X is S or O.

In a more preferred embodiment,
$R_1$–$R_6$ are, independently, hydrogen, methyl, ethyl, isopropyl, cyclohexyl, methoxy, or phenyl;
$R_7$–$R_8$ are methyl or branched $(C_3$–$C_4)$ alkyl;
$YR_9$ is Cl or Y is N and $R_9$ is $(C_1$–$C_4)$ dialkyl; and
X is S or O.

In a most preferred embodiment,
$R_1$–$R_6$ are hydrogen;
$R_7$–$R_8$ are methyl or isopropyl;
Y is N and $R_9$ is dimethyl; and
X is O.

The silylating reagents of the invention can be readily prepared using methods known in the art. For example, the reagents can be prepared from the corresponding o-substituted phenyl acetylene (Prey, Ber. Dtsch. Chemo Res. 76:156 (1943); Prey et al, Monatsch. Chem. 80:790 (1949)). The preparation involves acetylation, hydrosilation (Brook et al, J. Org. Chem. 55:3909 (1990)), followed by simultaneous deacylation and substitution (see the Example below).

Conditions suitable for effecting cleavage of the protecting group of the invention can be established by one skilled in the art based on the disclosure provided. It will be clear from the Example that follows that solvent selection is particularly important and that irradiation in the presence of a polar solvent, such as acetonitrile, is preferred. The wavelength of irradiation will vary with the protecting group. Typically, however, irradiation in the range of 250– 400 nm is effective.

The choice of protecting group for use in any particular synthetic application may vary depending, at least in part, on the stability required. It will be appreciated that, in certain applications, it will be advantageous to use a protecting group that will not be cleaved under conditions used to effect removal of other protecting groups. By way of example, it is noted that the instability of (hydroxystyryl)dimethylsilyl (HSDMS) ethers is comparable to simple trimethylsilyl ethers: tetrabutyl ammonium fluoride (TBAF) (5 equiv, THF, 10 min), 1N NaOH (5 equiv, THF, 30 min), and 1N HCl (5 equiv, THF, 10 min) remove it readily, but aqueous workup conditions do not harm it. Conversely, (hydroxystyryl)diisopropylsilyl (HSDIS) ethers have stability similar to TIPS ethers, since they survive tetrazole (the condensing catalyst for phosphoramidite-based DNA synthesis, 5 equiv, THF), EtMgBr(excess, 0° C., THF), $NaBH_4$ (excess, rt, MeOH and pyridinium dichromate (PDC) (excess, rt, $CH_2Cl_2$). They are removed by TBAF (5 equiv, THF, 20 min) and 1NHCl (5 equiv, THF, 20 min).

The photochemically-removable silyl protecting groups disclosed herein can be used in a wide variety of organic synthetic schemes. The styrylsilyl reagents are, for example, excellent for use in the protection of primary and secondary alcohols. Table 1, referenced in the Example below, illustrates the range of alcohols that can be protected using the present reagents. A similar range of thiol and amino groups (eg dimethylamine, aniline, N-methylaniline, N-methylacetamide, octanethiol, cystathionine and benzylmercaptan) can be protected using the disclosed styrylsilyl reagents.

The photochemically removable silyl protecting groups of the invention are suitable for use in light-directed, spatially addressed parallel chemical synthesis, a method that permits the preparation of very large arrays containing vast numbers of oligomeric molecules (see U.S. Pat. No. 5,143,854). These photoremovable silyl groups are particularly applicable to DNA synthesis since the linking group in DNA is a protected hydroxyl. The photochemically removable silyl groups of the invention can substitute for the dimethoxytrityl group typically used in automated DNA syntheses (Gait "Oligonucleotide Synthesis. A Practical Approach", IRL Press, Oxford, 1984).

Certain aspects of the present invention are described in greater detail in the non-limiting Example that follows (see also J. Org. Chem. 58:6961 (1993)).

EXAMPLE

Figure 1:
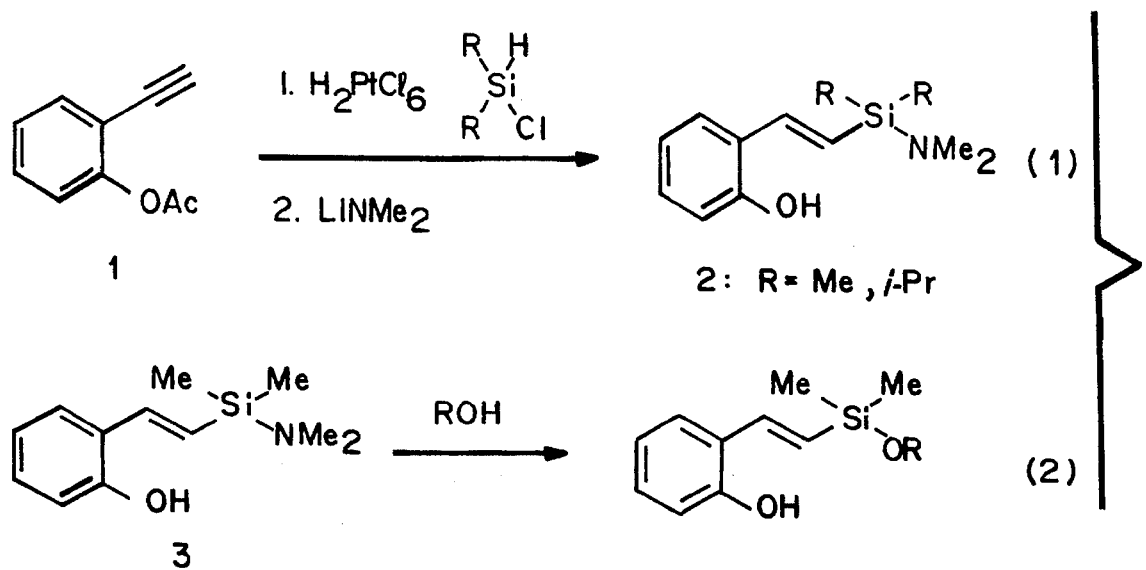
FIG. 1. Preparation of silylating reagent and use of reagent as alcohol protecting agent.

The silylating reagents "2" of FIG. 1 were prepared from o-hydroxyphenylacetylene by acetylation, hydrosilation (dimethyl- and diisopropylchlorosilane), and simultaneous deacylation and chloride substitution with lithium dimethylamide (70% overall) (see eq 1 of FIG. 1). Stirring an alcohol in THF with "2" (R=Me) converts it to the protected derivative within 3h (see eq 2 of FIG. 1). Protection with "2" (R=i-Pr) requires overnight reaction at room temperature, and in some cases warming. As shown in Table I, protection of primary and secondary alcohols occurs in excellent yields. Tertiary alcohol protection has not been effected. These silyl ethers show a strong short wavelength absorption band at 258 nm (log ε 4.28) and a weaker band at 309 nm (log ε 3.94).

TABLE I

Alcohols Protected with Reagents 2 and Their Deprotection Reactions

| compd | | protection (% yield, procedure A or B)[a] | deprotection (% yield, procedure C)[a] |
|---|---|---|---|
|  | 12 | 80,A | 83 |
| 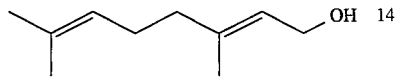 | 13 | 82,B | 87 |
| 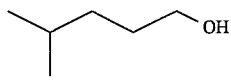 | 14 | 92,A | 91 |
|  | 15 | 95,A | 89 |
| 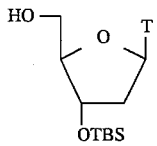 | 16 | 86,A | 84 |
| 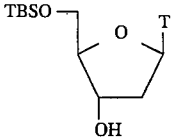 | 17 | 76,A[b] | 92[c] |
| 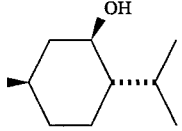 | 18 | 72,A[b] | 91[c] |
| 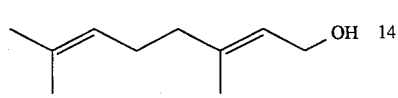 | 19 | 91,A | 87 |
|  | 14 | 70,B | 75 |

[a]Procedure A: The alcohol (1.2 mmol) was dissolved in 5 ml of THF and added to a solution of 1.0 mmol of "2" (R = Me) in THF. After 3 h at rt, TLC showed the reaction was complete.
Procedure B: The alcohol (1.2 mmol) was dissolved in 5 ml of THF and added to a solution of 1.0 mol of "2" (R = i-Pr) in THF. After 12 h at rt or 4 h at reflux, TLC showed the reaction was complete.
Deprotection procedure C: The silyl ether (30 mg) was dissolved in acetonitrile at a concentration of 0.01 M and irradiated in a quartz cell in the Rayonet reactor (254 nm) at rt for 30 min, when monitoring by TLC showed that the reaction was complete. Silica gel chromatography provided the starting alcohol in the indicated yields.
[b]Reflux, 4 h.
[c]40 min irradiation, >95% yield by NMR.

Irradition of "4" (Rayonet reactor, 254 nm, quartz reaction vessel) in acetonitrile produces "5" (84%) and the alcohol within 30 min (see eq 1 of FIG. 2). Using benzene, "4" is converted to the silylidene derivative "6" (91%) within 20 min (see eq 2 of FIG. 2).

Support for the proposed mechanism of deprotection was gained by study of a substrate that cannot form a cyclic siloxane such as "5". When "7" (isolated by silica gel chromatography as a byproduct in a preparation of "2" (R=i-Pr)) is irradiated in acetonitrile, cis isomer "8" is produced as the minor component of a 60:40 mixture within 30 min (see eq 1 of FIG. 3).

These reactions can be explained by two competing channels, one concerted and solvent independent, the other stepwise and highly solvent dependent. Deprotection may occur by an initial trans-cis isomerization to produce betaine "9", followed by elimination of alcohol, or by a photosolvolysis to generate the highly conjugated quinone methidesilaalkene "10", followed by proton transfer and electrocyclic ring closure (see eq 2 FIG. 3). Rearrangement may occur by an initial [1,5]-H shift to produce the quinone methide "11" followed by conformational change and a [1,5]-Si shift (see eq 3 of FIG. 3).

Table I summarizes the rapid (within 30 min) deprotection reactions of a variety of silyl ethers prepared from primary and secondary alcohols and compounds "2". High yields of purified material are uniformly observed despite the pilot scale on which these reactions have been conducted.

All documents cited above are hereby incorporated in their entirety by reference.

One skilled in the art will appreciate from a reading of this disclosure that various changes in form and detail can be made without departing from the true scope of the invention.

What is claimed is:

1. A photochemically-removable silyl protecting agent of the Formula (I):

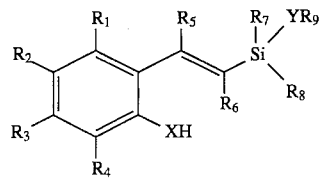

wherein:

$R_1$–$R_6$ are, independently, hydrogen, alkyl, O-alkyl, N-alkyl, S-alkyl, aryl, heteroaryl or halogen;

$R_7$–$R_8$ are alkyl;

$YR_9$ is a leaving group; and

X is S, O or NH;

or salt thereof.

2. The agent of claim 1 wherein $R_1$–$R_6$ are, independently, hydrogen, $(C_1$–$C_4)$alkyl, O-$(C_1$–$C_4)$alkyl, N-$(C_1$–$C_4)$alkyl, S-$(C_1$–$C_4)$alkyl, phenyl, Br or Cl;

$R_7$–$R_8$ are $(C_1$–$C_4)$ alkyl;

$YR_9$ is a halogen or Y is N, S or O and $R_9$ is $(C_1$–$C_4)$ alkyl or di$(C_1$–$C_4)$ alkyl, as appropriate; and X is S or O.

3. The agent according to claim 1 wherein $R_1$–$R_6$ are, independently, hydrogen, methyl, ethyl, isopropyl, cyclohexyl, methoxy, or phenyl;

$R_7$–$R_8$ are methyl or branched $(C_3$–$C_4)$ alkyl;

$YR_9$ is Cl or Y is N and $R_9$ is $(C_1$–$C_4)$dialkyl; and

X is S or O.

4. The agent according to claim 1 wherein $R_1$–$R_6$ are hydrogen;

$R_7$–$R_8$ are methyl or isopropyl;

Y is N and $R_9$ is dimethyl; and

X is O.

5. A method of protecting a reactive functional group comprising reacting said agent of claim 1 with said functional group under conditions such that a styrylsilyl derivative of said functional group is formed.

6. The method according to claim 5 wherein said functional group is an alcohol, thiol or amino group.

7. The method according to claim 6 wherein said functional group is a primary or secondary alcohol.

8. A compound of formula

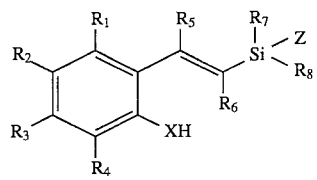

wherein $R_1$–$R_8$ and X are as defined in claim 1 and wherein Z is derived from an alcohol, thiol or amine and is covalently linked to the silicon atom via the oxygen, sulfur or nitrogen atom thereof, respectively.

9. The compound according to claim 8 wherein said compound is a (hydroxystyryl)dialkylsilyl ether, amine or sulfide.

10. The compound according to claim 9 wherein said compound is a (hydroxystyryl)di$(C_{1-4})$alkylsilyl ether.

* * * * *